(12) United States Patent
Canfield et al.

(10) Patent No.: US 11,094,138 B2
(45) Date of Patent: *Aug. 17, 2021

(54) SYSTEMS FOR LINKING FEATURES IN MEDICAL IMAGES TO ANATOMICAL MODELS AND METHODS OF OPERATION THEREOF

(71) Applicant: KONINKLIJKE PHILIPS N.V., Eindhoven (NL)

(72) Inventors: Earl M. Canfield, Snohomish, WA (US); Wendy Mei Yee, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/204,251

(22) Filed: Nov. 29, 2018

(65) Prior Publication Data
US 2019/0096140 A1    Mar. 28, 2019

Related U.S. Application Data

(63) Continuation of application No. 15/303,366, filed as application No. PCT/IB2015/052899 on Apr. 21, 2015, now Pat. No. 10,176,645.
(Continued)

(51) Int. Cl.
*G06T 7/00*        (2017.01)
*G06T 19/20*       (2011.01)
(Continued)

(52) U.S. Cl.
CPC ............. *G06T 19/20* (2013.01); *A61B 8/06* (2013.01); *A61B 8/0891* (2013.01); *A61B 8/468* (2013.01);
(Continued)

(58) Field of Classification Search
None
See application file for complete search history.

(56) References Cited

U.S. PATENT DOCUMENTS

| 2004/0162483 | A1* | 8/2004 | Kimura | G01R 33/56308 |
| | | | | 600/419 |
| 2007/0078343 | A1* | 4/2007 | Kawashima | A61B 8/5238 |
| | | | | 600/443 |

(Continued)

FOREIGN PATENT DOCUMENTS

EP    1720038 A2    11/2006

OTHER PUBLICATIONS

Brelstaff, et al., "Internet Patient Records: new techniques", Journal of Medical Internet Research, published online Mar. 1, 2017 3(1), 15 pages.

*Primary Examiner* — Robert J Craddock

(57) ABSTRACT

A medical imaging system configured to link acquired images to markers or tags on an anatomical illustration, based, at least in part on spatial and anatomical data associated with the acquired image. The medical imaging system may be further configured to generate a diagnostic report including the anatomical illustration containing the markers. The diagnostic report may allow a user to select a marker to view information associated with an acquired image and/or the acquired image. Multiple images may be associated with a marker, and/or multiple markers may be associated with an image. A set of 2D and/or 3D anatomical illustrations may be generated which contains markers from multiple diagnostic reports and updated automatically for an individual patient's anatomical model by the application to reflect measurements and/quantitative findings related to organ, tissue, and vessel size, location, deformation, and/or obstruction.

12 Claims, 11 Drawing Sheets

Related U.S. Application Data

(60) Provisional application No. 61/987,512, filed on May 2, 2014.

(51) Int. Cl.

| | | |
|---|---|---|
| *A61B 8/08* | (2006.01) | |
| *A61B 8/00* | (2006.01) | |
| *G06F 19/00* | (2018.01) | |
| *A61B 8/06* | (2006.01) | |
| *G16H 40/63* | (2018.01) | |
| *G16H 30/20* | (2018.01) | |
| *G16H 30/00* | (2018.01) | |

(52) U.S. Cl.
CPC .............. *A61B 8/483* (2013.01); *A61B 8/488* (2013.01); *A61B 8/5238* (2013.01); *A61B 8/5292* (2013.01); *G06F 19/00* (2013.01); *G06F 19/321* (2013.01); *G16H 30/00* (2018.01); *G16H 30/20* (2018.01); *G16H 40/63* (2018.01); *G06T 7/0012* (2013.01); *G06T 2200/04* (2013.01); *G06T 2207/10136* (2013.01); *G06T 2207/30024* (2013.01); *G06T 2207/30104* (2013.01); *G06T 2207/30204* (2013.01)

(56) References Cited

U.S. PATENT DOCUMENTS

| | | |
|---|---|---|
| 2008/0101667 A1 | 5/2008 | Begelman et al. |
| 2010/0164950 A1* | 7/2010 | Zhao .................... G06T 11/00 345/419 |
| 2012/0143090 A1 | 6/2012 | Hay et al. |
| 2012/0210204 A1 | 8/2012 | Kramer et al. |
| 2013/0184584 A1* | 7/2013 | Berkey ................ A61B 8/5292 600/441 |
| 2013/0211230 A1 | 8/2013 | Spelling |
| 2013/0231564 A1 | 9/2013 | Zagorchev et al. |
| 2013/0324841 A1 | 12/2013 | Kamen et al. |

\* cited by examiner

SYSTEMS FOR LINKING FEATURES IN MEDICAL IMAGES TO ANATOMICAL MODELS AND METHODS OF OPERATION THEREOF

CROSS-REFERENCE TO RELATED APPLICATIONS

This application is a continuation of U.S. application Ser. No. 15/303,366, filed Oct. 11, 2016, which issued as U.S. Pat. No. 10,176,645, which is the U.S. National Phase application under 35 U.S.C. § 371 of International Application No. PCT/IB2015/052899, filed Apr. 21, 2015, which claims the benefit of Provisional Application Ser. No. 61/987,512, filed May 2, 2014. These applications are hereby incorporated by reference herein.

The present system relates generally to a medical imaging system and more particularly, to an imaging system for implementing an dynamic tagging technique for anatomical models of a patient, and a method of operation thereof.

After an imaging technician completes an imaging exam, the imaging technician prepares a diagnostic report based on the images acquired during the exam. Images of a patient's heart, vasculature, liver, breast, or other anatomical region of interest may be acquired during the exam, for example. The diagnostic report may include patient demographic information followed by sorted groups of anatomical numeric data and findings. For example, the imaging technician may have measured the width of the left and right carotid arteries during an ultrasound exam. The imaging technician would include these measurements in the diagnostic report. The imaging technician may also indicate any plaque seen in the ultrasound images in the diagnostic report. In addition to the written findings, the imaging technician may submit digital or printed worksheets that contain simple drawings of anatomy relevant to the exam. Continuing with the present example, the imaging technician may mark the locations of the indicated plaque and where the width measurements were taken on a drawing of the carotid arteries. These worksheets may be in digital format or they may be paper copies that the imaging technician fills in by hand. The completed diagnostic report may be kept in hard copy in a patient's medical record or stored in digital format in a patient's electronic medical record. The acquired images may be printed or also stored in a patient's electronic medical record.

Once the imaging technician has completed the diagnostic report, it may be sent to a physician for review who may or may not have experience in interpreting medical images. The physician may have access to both the diagnostic report and the acquired images. However, the physician may not know which images or what portion of the images the imaging technician observed the medical findings or took measurements. The images may also lack a direct spatial linking with key anatomical structures of the patient. Furthermore, the physician may need to manually search through the images to find the features noted by the imaging technician in the diagnostic report. Correlating the imaging technician's report to the images may become more difficult when anatomical structures vary widely from the drawings of anatomy or the structures are located close together in the images.

The process of producing a diagnostic report described above is time intensive. The imaging technician produces the diagnostic report after the exam has been completed. The imaging technician may need additional software to draft the written findings and annotate the drawings of anatomy. The imaging technician may further need to locate paper copies of the drawings to annotate by hand. These paper copies must then be manually associated with the patient's medical record and the correct exam. As discussed above, the physician may have difficulties correlating the findings in the diagnostic report to the images. In the case of hand-written reports, the physician may have difficulty reading the imaging technician's hand writing. These difficulties may lead to increased time for generating and interpreting diagnostic reports and may also reduce the ability of the physician to make a proper diagnosis.

According to one illustrative embodiment of the invention disclosed, a medical imaging system may include a first non-transitory computer readable storage medium containing spatial data associated with an image, a second non-transitory computer readable storage medium containing a dataspace, an anatomical information processor may be configured to receive the spatial data and data associated with the dataspace and convert the spatial data to data associated with the dataspace and link the image to the data associated with the dataspace, and a third non-transitory computer readable storage medium may be configured to store the image and data converted by the anatomical information processor. The anatomical information processor may be further configured to link measurements associated with the image to the data associated with the dataspace. The dataspace may include data associated with human anatomy as well as diagnostic notes and measurements. The medical imaging system may further include a graphics processor capable of rendering an illustration from the dataspace. The imaging system may also comprise an ultrasound probe for acquiring the image. The anatomical information processor may be further configured to modify the dataspace based on spatial data associated with the image. The spatial data may be compliant with the DICOM standard.

According to another disclosed embodiment of the present invention, a method of linking data in a medical imaging system may include generating, with a processor, a computer-readable code that describes spatial data associated with an image; converting, with the processor, the computer-readable code into a marker, wherein the marker is computer-readable information relating to a dataspace; and linking, with the processor, the image with the marker. The method may further include generating, with the processor, a computer-readable code that describes spatial data associated with a measurement associated with the image; converting, with the processor, the computer-readable code associated with the measurement into the marker; and linking, with the processor, the measurement with the marker. The method may further include linking an additional image to the marker. The spatial data and dataspace used in the method may contain data relating to human anatomy. The method may further include rendering, with a graphics processor, an illustration from the dataspace and displaying the illustration on a displayed, with the marker displayed on the illustration. The method may further include saving, on a non-transitory computer-readable medium, the image and the marker; generating, with the processor, a diagnostic report, wherein the diagnostic report includes the image and the marker; and saving, on the non-transitory, computer-readable medium, the diagnostic report. The diagnostic report may be accessed with a computer, wherein the computer accesses the diagnostic report on the non-transitory computer-readable medium via a secure Internet connection. According to a further disclosed embodiment of the present invention, a medical imaging system may be configured to generate code corresponding to spatial information associated with an acquired image; convert the code corresponding to spatial information to code for a marker associated with a dataspace; and link the acquired image with the marker. The medical imaging system may be further configured to generate code corresponding to spatial information associated with a measurement made on the acquired image; convert the code corresponding to the spatial information associated with the measurement to code for the marker associated with the data space, and link the measurement with the marker.

The medical imaging system may further be configured to alter the dataspace corresponding to spatial information associated with the acquired image. The medical imaging system may be further configured to render an illustration based on the dataspace; display the marker on the illustration, and display the acquired image when a user selects the marker in the illustration. The medical imaging system may further be configured to save the link, the acquired image, and the marker in a non-transitory computer-readable medium as a diagnostic report. A user may access the diagnostic report and make an additional measurement on the acquired image. A user may further be able to access the diagnostic report and make a modification to the measurement. The medical imaging system may include an ultrasonic probe configured to acquire the image.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

In some embodiments, there are provided a system, application, and/or method for automatically generating a diagnostic report or a portion of a diagnostic report from findings or measurements made on medical images so as to standardize medical image reporting, which may reduce preparation times, evaluation times, and errors. The present invention includes, for example, associating measurements (e.g., from ultrasound images) with an anatomical model representing a patient's anatomy including, e.g., various body parts, such as tissues, organs, musculoskeletal tissue and/or blood vessels. Costs for acquiring, reporting, and/or evaluating medical images may be reduced. Diagnoses and/or evaluation of treatment efficacy may also be improved. In addition, the present invention provides several other useful aspects. For example, the systems and methods of the present invention further include dynamic updating of the actual dimensions of the patient's anatomy in real-time or after image acquisition to show the patient's features as they have been recorded and subsequently measured in an image, such as an ultrasound image. These features of the present invention provide a dynamic representation of a patient's actual anatomical dimensions in the form of a 3D anatomical model that is stored digitally and can be readily reviewed by physicians and other medical practitioners alike. Furthermore, the automatic or manually initiated adjustment of the anatomical model can be used, e.g., with measuring blood vessels with artheroschlerotic plaques or organ sizing as well.

Figure 1:
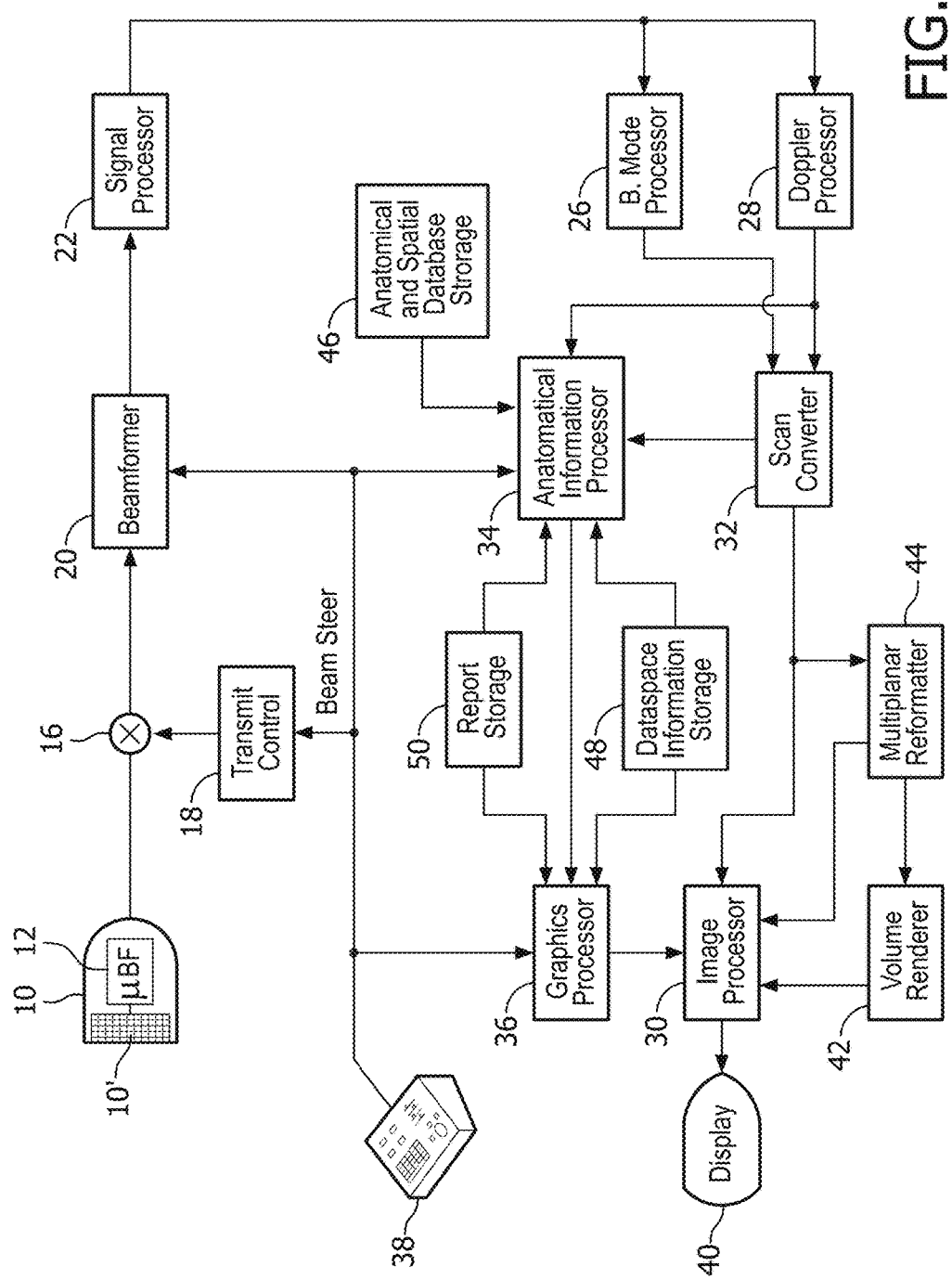
FIG. 1 is a schematic view of an embodiment of an ultrasound imaging system according to the present system.

Referring to FIG. 1, an ultrasound imaging system constructed in accordance with the principles of the present invention is shown in block diagram form. Although an ultrasound imaging system is shown in explanatory examples of embodiments of the invention, embodiments of the invention may be practiced with other medical imaging modalities. Other modalities may include, but are not limited to, magnetic resonance imaging and computed tomography. In the ultrasonic diagnostic imaging system of FIG. 1, a transducer array 10' is provided in an ultrasound probe 10 for transmitting ultrasonic waves and receiving echo information. The transducer array 10' is preferably a two dimensional array of transducer elements capable of scanning in three dimensions, for instance, in both elevation and azimuth about the location of the mitral valve, for 3D imaging. The transducer array is coupled to a microbeamformer 12 in the probe which controls transmission and reception of signals by the array elements. The microbeamformer is coupled by the probe cable to a transmit/receive (T/R) switch 16 which switches between transmission and reception and protects the main beamformer 20 from high energy transmit signals. The transmission of ultrasonic beams from the transducer array 10 under control of the microbeamformer 12 is directed by the transmit controller 18 coupled to the T/R switch and the beamformer 20, which receives input from the user's operation of the user interface or control panel 38. One of the functions controlled by the transmit controller is the direction in which beams are steered. Beams may be steered straight ahead from (orthogonal to) the transducer array, or at different angles for a wider field of view. The partially beamformed signals produced by the microbeamformer 12 are coupled to a main beamformer 20 where partially beamformed signals from the individual patches of elements are combined into a fully beamformed signal.

The beamformed signals are coupled to a signal processor 22. The signal processor 22 can process the received echo signals in various ways, such as bandpass filtering, decimation, I and Q component separation, and harmonic signal separation. The signal processor may also perform additional signal enhancement such as speckle reduction, signal compounding, and noise elimination. The processed signals are coupled to a B mode processor 26 and a Doppler processor 28. The B mode processor 26 employs amplitude detection for the imaging of structures in the body such as a tumor. The Doppler processor 28 processes temporally distinct signals from tissue and blood flow for the detection of the motion of substances such as the flow of blood cells in the image field. The structural and motion signals produced by the B mode and Doppler processors are coupled to a scan converter 32 and a multiplanar reformatter 44. The scan converter 32 arranges the echo signals in the spatial relationship from which they were received in a desired image format. For instance, the scan converter 32 may arrange the echo signal into a two dimensional (2D) sector-shaped format, or a pyramidal three dimensional (3D) image. The scan converter 32 can overlay a B mode structural image with colors corresponding to motion at points in the image field corresponding with their Doppler-estimated velocities to produce a color Doppler image which depicts the motion of tissue and blood flow in the image field. The multiplanar reformatter 44 can convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point, e.g., as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40.

In accordance with the principles of the present invention, 2D or 3D images are coupled to the anatomical information processor 34. The anatomical information processor 34 operates as described below to encode anatomical location information from the images acquired with the ultrasound system. The anatomical information processor 34 may receive input from the user control panel 38, such as the type of exam performed and which standard view is being acquired. Output data from the anatomical information processor 34 is coupled to a graphics processor 36 for the reproduction of output data from the processor with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of a display of multiple multiplanar reformatted (MPR) images.

The anatomical information processor 34 may retrieve spatial and anatomical data relating to the images acquired by the imaging system. This data may be calculated in real time by the imaging system by an anatomical image processor (not shown), an example of which can be found in patent application PCT/IB2011/053710, "Automated three dimensional aortic root measurement and modeling." Other image analysis methods may also be used to obtain the spatial and anatomical data from the acquired images. In another embodiment, the spatial and anatomical data for standard views taken during routinely prescribed imaging exams may be stored in a database 46 accessible to the anatomical information processor 34. The stored data may be compliant with a standard, for example, the Digital Imaging and Communications in Medicine (DICOM) standard. The DICOM standard includes a meta tag that may enable a specific diagnostic code, either for diagnostic outcomes tracking or medical billing purposes.

The anatomical information processor 34 may access storage containing information relating to a dataspace 48. The dataspace may be 2D or 3D. In some embodiments, the dataspace includes data representing an anatomical model of human anatomy, and a 2D or 3D illustration of human anatomy may be rendered from the data of the dataspace. As described further herein, the anatomical model can be provided with standard dimensions and measurements and other information can be linked directly to the anatomical model. Moreover, when sufficient 3D data is available from ultrasound quantification tools and/or measurement applications, the present invention can automatically render or redraw the presence, outline, location, and relative anatomical volume of the place to scale relative to the patient's spatial anatomical model. For example, the dimensions of the anatomical model can be updated automatically or manually to represent actual measurements and dimensions of a particular patient based on the imaging data, e.g., from a 3D ultrasound image. In one embodiment, a user can measure the actual dimensions of the patient's anatomy and then the anatomical information processor 34 can update the dimensions of the anatomical model accordingly. Alternatively, the anatomical information processor 34 can also be configured to calibrate the dataspace and the acquired images to automatically update the dimensions of the anatomical model in accordance with actual dimensions of the patient's anatomy. In general, the manual or automatic updating of the anatomical model can be applied to any anatomy that can be imaged, e.g., by ultrasound imaging techniques. For example, a patient's heart, blood vessels, liver, kidney, and other organs can be measured, displayed, reported, and/or used to update the anatomical model in the diagnostic reports for real-time or later review by a user. Real-time images can be generated and included in the diagnostic report along with the anatomical model. In some embodiments, the images can be generated over time to allow for additional information with respect to data trends, such as shrinkage or growth of certain regions of interest (e.g., a tumor) of a patient's anatomy.

An example dataspace of human anatomy may be provided by 3D anatomical modeling companies that support unique spatial identifiers within those anatomical dataspaces, but other dataspaces may be used. The rendering may be performed by the graphics processor 36 and displayed on the display 40. The rendered illustrations of human anatomy may replace the worksheets currently used in diagnostic reports. The anatomical information processor 34 may be capable of performing a conversion between the spatial and anatomical data associated with the acquired images and the data associated with the dataspace. The anatomical information processor 34 may further link the acquired image or images associated with the data associated with the dataspace. Series of images that may be displayed sequentially, comprising a time-elapsed loop or "movie," may also be linked. The anatomical information processor 34 may also be capable of performing a conversion between the data associated with the dataspace and the spatial and anatomical data associated with the acquired images. The anatomical information processor 34 may further link the data associated with the dataspace to the corresponding acquired image or images. The linking processes described may also be referred to as tagging. The links, images, and other information may be saved by the anatomical information processor 34 in a report storage 50. The report storage 50 may be accessible to the anatomical information processor 34, the graphics processor 36, the user control panel 38, other elements of the imaging system 100, and/or a remote computer terminal (not shown).

When a measurement or other notation is made on an acquired image, the anatomical information processor 34 may automatically link the measurement or other notation and the associated acquired image with a marker or tag associated with the dataspace. In some examples, a DICOM meta tag or other information may be linked to the dataspace. In some embodiments, a DICOM meta tag can also include a specific diagnostic code, either for diagnostic outcomes tracking or medical billing purposes, which could be linked with the presence of a pin or other marker in the dataspace. The marker includes information which may cause it to appear in the corresponding anatomical place in the anatomical model representing the patient's anatomy, which corresponds to the anatomical location where the image was acquired. The link may be dynamic in that any changes to the measurement and/or notation are propagated to the marker, and any changes made to the marker are propagated back to the measurement and/or notation. In addition, the relationship of the spatial marker to the medical image and the overall anatomical model of the patient's anatomy can be viewed from multiple perspectives (pre-set or freehand) that are controlled by the user's "virtual camera" perspective. The user can view multiple perspectives and directly manipulate their perspective of the same spatial marker relative to the ultrasound data set and anatomical model through a variety of interaction methods (touch screen interactions, movements, and gestures; non-surface hand gestures and movements; computer controllers based on eye-tracking technology; trackballs; trackpads; computer mice; keyboard controls). Moreover, the system may further update the dimensions of the anatomical model to represent the actual measured dimensions of the patient's anatomy, as described herein.

In some embodiments of the present invention, additional information about the patient's anatomy can be provided and linked and/or further displayed on an anatomical model. In one embodiment, one or a sequence of elastography images (elastograms) can be acquired with an ultrasound probe, which is used to vary the pressure and compress a region of interest of an anatomic mass within the body. A region of interest can be identified in one or more of the images and then linked to the anatomical model to provide further information about the tissue. For example, a liver can be scanned and displayed in the anatomical model, and an associated elastogram can be linked to the region of the liver containing a lesion that shows different strain data than surrounding healthy tissue in the liver. Moreover, the region showing different strain can be overlaid on the anatomical model to identify to a physician where the lesion may be located with respect to the remained of the liver. In another embodiment, volume deformations can be depicted and identified with the anatomical model. For example, a portion of the patient's kidney may be imaged and measured. After measuring the kidney, it may become apparent that the kidney tissue is deformed. This deformation can be manually or automatically integrated with the anatomical model to show the actual dimensions of the deformation. Furthermore, a marker can be linked to the location of the anatomical model to provide further information about the deformation to a user reviewing the diagnostic report.

Figure 2:
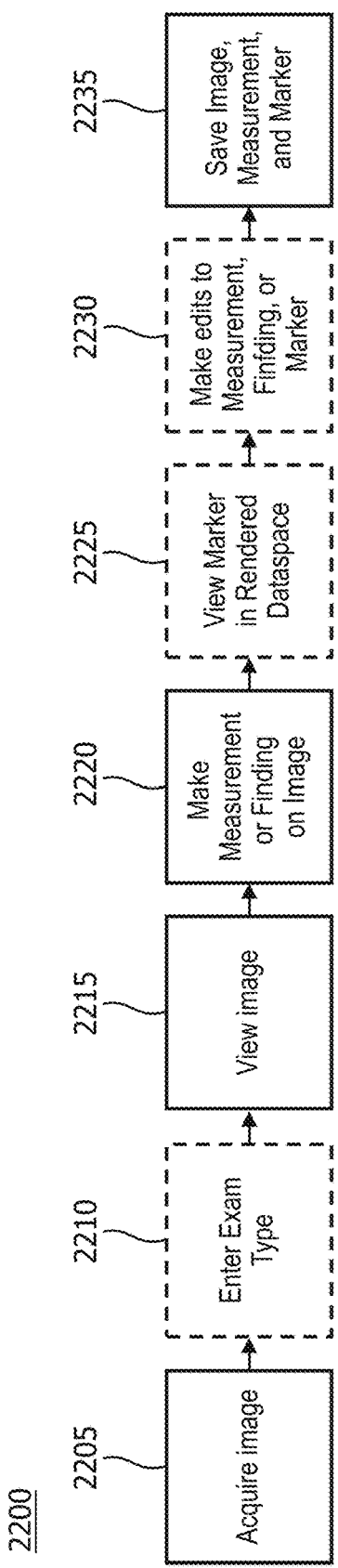
FIG. 2 is a block diagram of a process performed by an imaging technician according to an embodiment of the present system.

In an exemplary embodiment of the invention, an imaging technician may perform a process 2200 as illustrated in the flowchart in FIG. 2. In an example, a sonographer may acquire an image from a patient at 2205 with the imaging system depicted in FIG. 1. The sonographer may optionally use the user interface 38 to indicate the type of exam being conducted and the view being acquired at 2210. The sonographer may view the acquired image on the display 40 at 2215. The sonographer may take a measurement on the acquired image at 2220 with the user interface 38. The measurement taken by the sonographer may be automatically processed by the anatomical information processor 34 and a corresponding marker in the dataspace is generated for that measurement and linked to the acquired image. Optionally, the sonographer may open a window on the display 40 that may show a 2D or 3D rendering of the human anatomy associated with the dataspace in the dataspace information storage 48, the rendering performed by the graphics processor 36. The sonographer may view the marker in the 2D or 3D rendering of the human anatomy, i.e., an anatomical model, that corresponds to the measurement the sonographer made in the acquired image at 2225. As described herein, the dimensions of the anatomical model can be dynamically updated manually or automatically to represent the actual dimensions of the human anatomy that was imaged. In some embodiments, the acquired image and rendered dataspace may be viewed at the same time. The sonographer may then edit the measurement and/or marker if desired. Edits made on the measurement or the marker may be automatically propagated to the other. If desired, the sonographer may make multiple measurements on the acquired image, which may cause multiple markers to be generated by the anatomical information processor 34. The sonographer may then save the acquired image, which may also save the measurement and marker to the report storage 50. The sonographer may save the images and measurements without having viewed the corresponding markers in the rendering of human anatomy as the marker is automatically generated and associated with the image by the anatomical information processor 34. The sonographer may also note a feature of interest at 2220, which may also be referred to as a finding, in the acquired image. Examples of findings include lesions, plaques, and blockages. The sonographer may select the desired portion of the image and place a finding indicator. The sonographer may add text associated with the finding and/or a graphical notation. The finding indicator may be converted to a marker in the dataspace in a similar process to the measurement described above. In this manner, the sonographer may generate markers or tags on an anatomical illustration with findings indicated on the illustration for use in a diagnostic report as the measurements and findings are being acquired. This may reduce the time necessary for the sonographer to prepare the diagnostic report and may also reduce errors in the diagnostic report. However, the sonographer may not be limited to generating the diagnostic report during the exam. The sonographer may be able to open images on the imaging system, stored in the report storage 50, associated with a past exam and add additional measurements, findings, or edit previously made measurements or findings. That is, the sonographer may start process 2200 at 2215. As noted above, it may be possible to eliminate other steps from process 2200 or modify the order of the steps performed in process 2200 without departing from embodiments of the invention. After opening images which contain these spatial markers, measurements, and notations, the user is also able to compare images from multiple exams to monitor patient progression before, during, and after surgical and/or therapeutic treatment.

Figure 3:
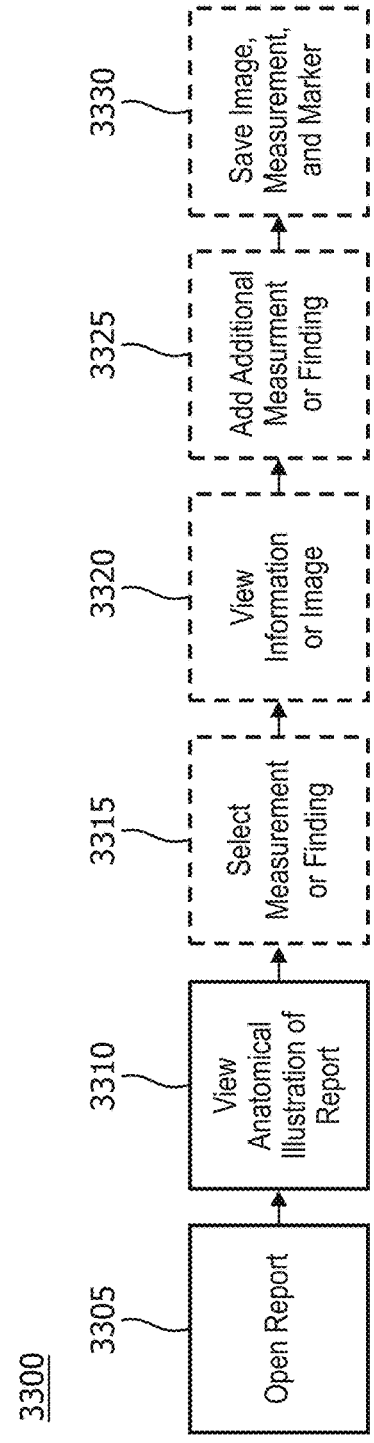
FIG. 3 is a block diagram of a process performed by a reviewer according to an embodiment of the present system.

In accordance with the principles of the present invention, a diagnostic report may be reviewed following a process 3300 illustrated in FIG. 3. In an example, a reviewing physician may open the diagnostic report at 3305 from the report storage 50 using the user interface 38 on the imaging system shown in FIG. 1, or the information from the diagnostic report may be uploaded from the report storage 50 to a computer system in a hospital and accessed from a computer terminal in the hospital, another computer, or mobile data device connected to the diagnostic report through a secure Internet connection (not shown). Other methods of accessing the diagnostic report may also be used. The physician may view the rendered anatomical illustration portion of the diagnostic report at 3310 on display 40, or other display device, and see markers where the sonographer made measurements or findings. The locations of the findings and measurements may be indicated by "x," circles, or other symbols on the anatomical illustration. Different types of measurements or findings may be indicated with different symbols. For example, locations where blood vessel width measurements were taken may be marked with an "x," and locations where the sonographer identified plaques may be marked with an "o." The physician may be able to select at 3315 a desired measurement or finding to display more information, such as the value of the measurement or a text note written by the sonographer. Other information may also be displayed when the physician selects a marker. The physician may further be able to select a desired measurement or finding at 3320 to open the image, images, or loop associated with the selected measurement or finding on the display 40 or other display device. Selection may be through the user interface 38, a touch screen, or other selection device. In some embodiments, the physician may be able to add additional measurements or findings to the diagnostic report at 3325 with the user interface 38 or other interface. The physician may make additions to the acquired images or in the anatomical illustrations. The additions in the acquired images may automatically be linked to markers in the dataspace, and additions to the markers may automatically be linked to the acquired images. The physician may be able to save the modified diagnostic report at 3330 to the report storage 50 or to another computer-readable medium. In some embodiments, the physician may be able to compare images from multiple exams to monitor patient progression before, during, and after surgical and/or therapeutic treatment.

Figure 4:
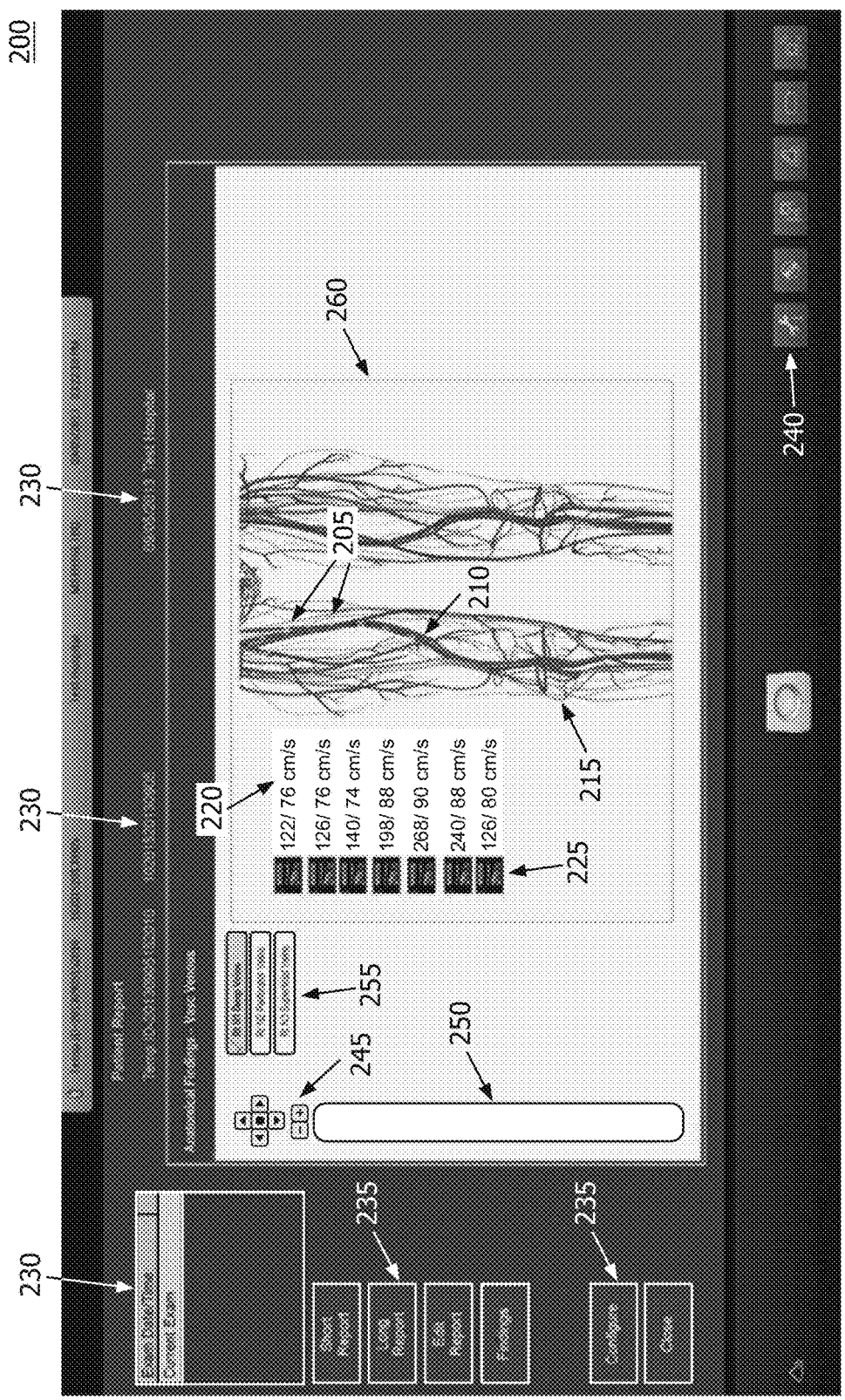
FIG. 4 is a screen shot of an example diagnostic report according to an embodiment of the present system.

An example of an anatomical illustration 260 portion of a diagnostic report is shown in a screen shot 200 in FIG. 4. In this embodiment, the diagnostic report is retrieved from the report storage 50 and viewed on the display 40 in a reporting software tool on the ultrasound system used to acquire the images. In this example, multiple measurements of blood flow velocity, including peak systolic velocity and end diastolic velocity, have been acquired from the Doppler information provided by the Doppler processor 28 along a blood vessel 210 in a leg 215 from an image or a series of images. Each measurement site 205 is marked on the illustration 260 with a circle on the blood vessel. Each circle has a corresponding tab 220 to the left. The tabs 220 display text indicating the type of measurement taken and the value of the measurement. To the left of the tabs 220 are icons 225 which correspond to the image from which the measurement was acquired. A user, such as a reviewing physician, may select the desired icon 225 and the corresponding image would be opened for viewing (not shown in FIG. 4). Time elapsed loops may also be associated with the icons. The diagnostic report may include fields for patient, exam, and hospital data 230, and display access to report formatting tools 235, and imaging system functions 240. The diagnostic report may further include controls 245 for zooming, panning, and rotating the anatomical illustration 260. There may also be tools 250 to allow a user to be able to select additional anatomical systems to display (e.g., muscles, skeletal system), or tools 255 to select and deselect subsystems from display (e.g., only veins, not arteries).

Figure 5:
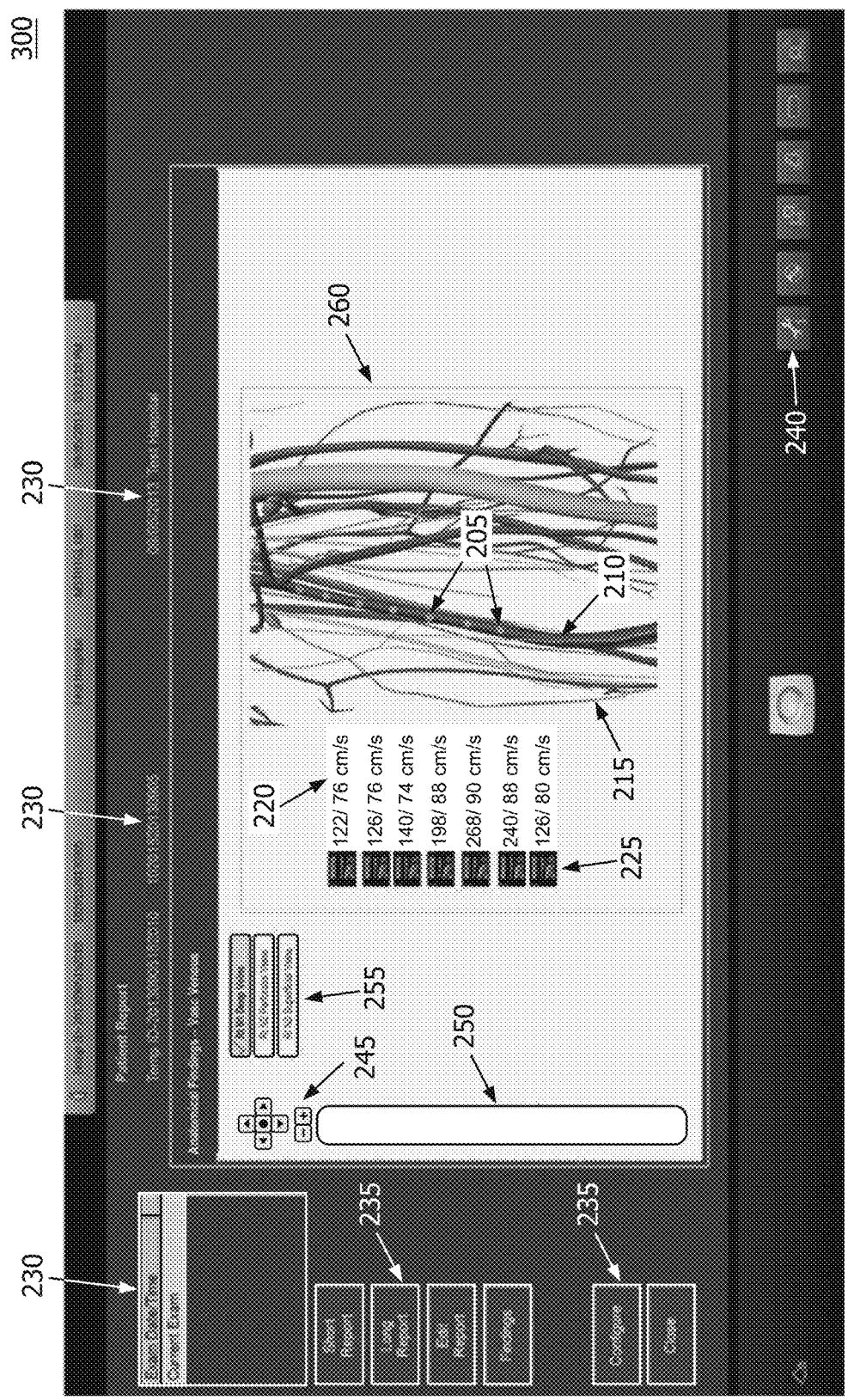
FIG. 5 is another screen shot of the example diagnostic report in FIG. 2 according to an embodiment of the present system.

The user may navigate through the rendered illustration 260 of the diagnostic report. The relationship of a marker to a medical image and the overall model of the patient's anatomy may be viewed from multiple perspectives. The perspectives may be pre-set or manually chosen by the user. The perspectives may be controlled by a "virtual camera" control, which may allow the user to zoom in and out or pan through the rendering. For example, the user may rotate or zoom in on a portion of the illustration as shown in screen shot 300 in FIG. 5. The user may view multiple perspectives and manipulate their perspective of the marker relative to the ultrasound data set and anatomical model through a variety of interaction methods. Interaction methods may include touch screen interactions, movements, and gestures, non-surface hand gestures and movements, computer controllers based on eye-tracking technology, trackballs, trackpads, computer mice, and keyboard controls. If the imaging technician indicated the type of exam and view being acquired, only the physiological system of interest may be rendered such that the markers of interest are not obscured by other systems (e.g., lymph, musculoskeletal) automatically. The user may further eliminate anatomical features that are not of current interest. As shown in FIGS. 4 and 5, as indicated by the tools 255 in the upper left, the user has chosen to only view Deep Veins.

Figure 6:
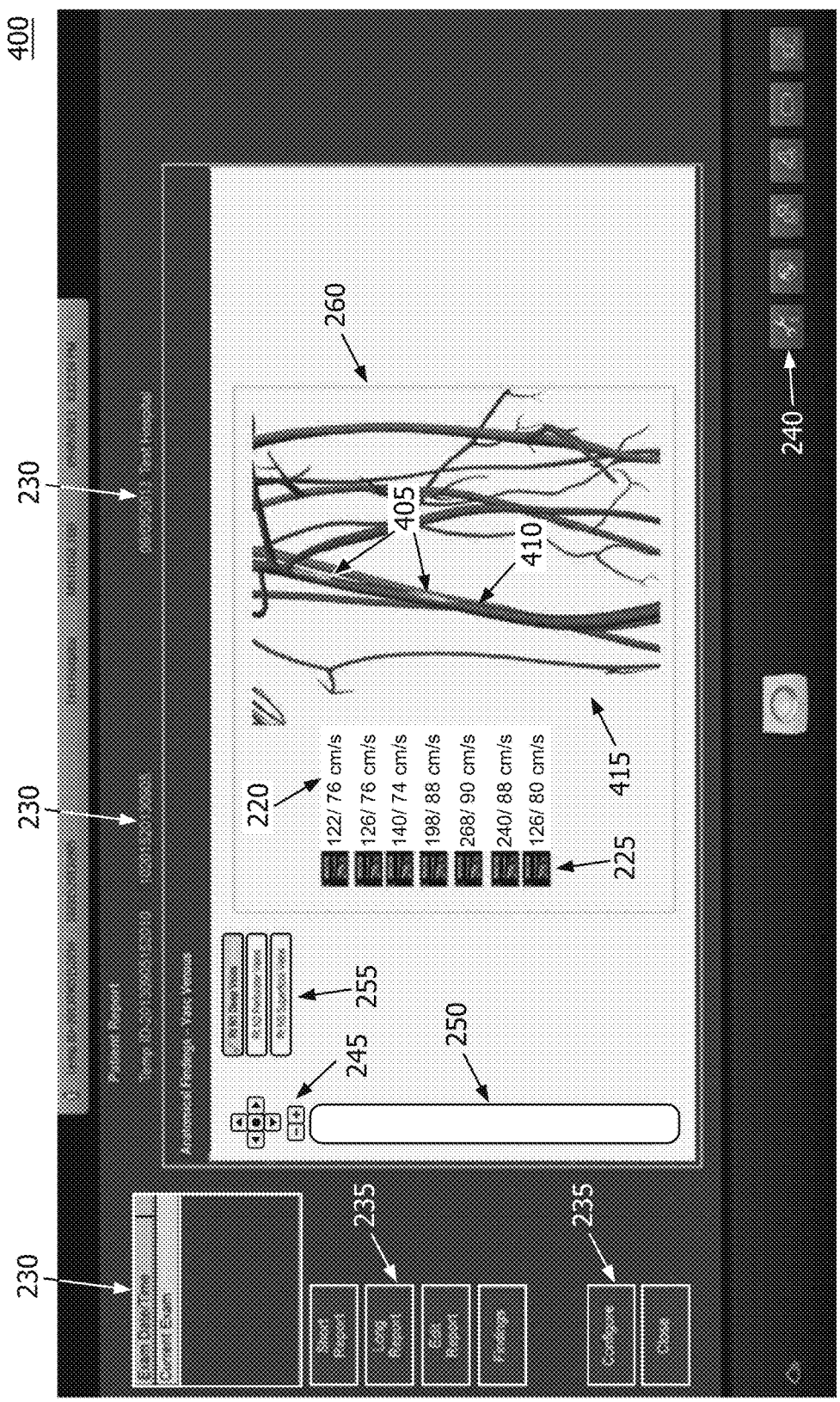
FIG. 6 is a further screen shot of the example diagnostic report in FIG. 2 according to an embodiment of the present system.

Other graphical indicators may be used to designate different measurements or findings in the anatomical illustration 260. FIG. 6 illustrates an example screen shot 400 of a diagnostic report. In this example, the imaging technician has indicated the location of two plaques 405 in a blood vessel 410 in a leg 415. The plaques 405 are designated by oblong regions rather than circles. Other symbols may be used to illustrate markers corresponding to different findings or measurements. Furthermore, as described herein, when sufficient 3D data is available from ultrasound quantification tools and/or measurement applications, the invention may automatically render or redraw the presence, outline, location, and relative anatomical volume of the feature of interest to scale relative to the patient's spatial anatomical model. Other symbols may be used to illustrate markers corresponding to different findings or measurements. In the context of this example, the system may automatically determine the location and volume of vascular plaques in the acquired images and render an illustration of the plaques in the anatomical illustration 260. Although an example of vascular plaques is described, other anatomical features or indicators may be determined and automatically rendered visually in the anatomical illustration 260. For example, tumor lesions, tissue stiffness, and/or flow rates may be determined. Visual rendering may include symbols, numerical values, color coding of organ illustrations, or other visual indicators of the determined features.

Figure 7:
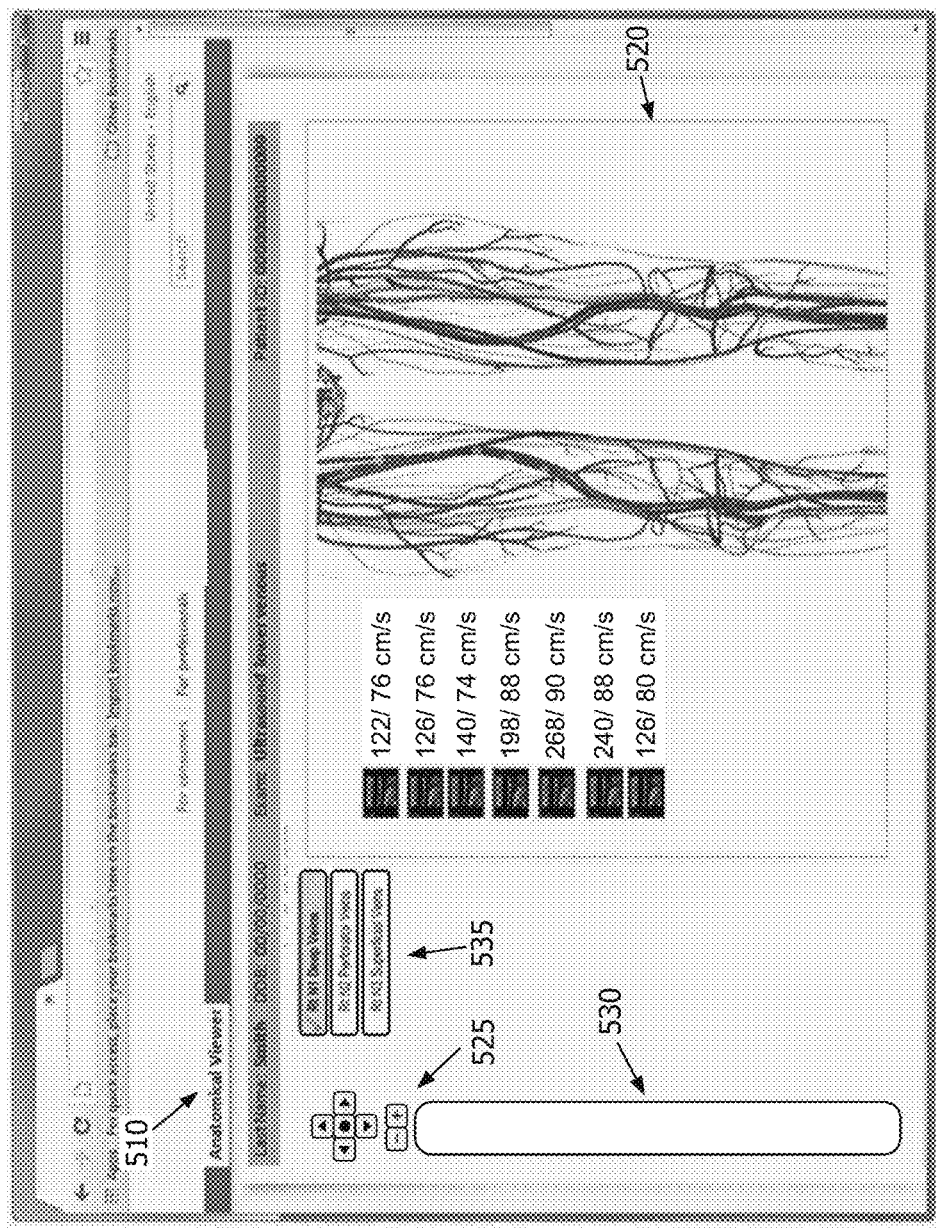
FIG. 7 is a screen shot of another example diagnostic report according to an embodiment of the present system.

FIG. 7 shows an example screen shot 500 of viewing a diagnostic report on a secure web interface 510. The software and/or web interface may have an anatomical illustration 520 similar to the interface illustrated in FIGS. 4-6. The web interface 510 may provide controls 525 for zooming, panning, and rotating the anatomical illustration 520. There may also be tools 530 to allow a user to be able to select additional anatomical systems to display (e.g., muscles, skeletal system), or tools 535 to select and deselect subsystems from display (e.g., only veins, not blood vessels). Although the user may be able to access the measurements and acquired images linked to the anatomical illustration 520, in some embodiments, the web interface 510 may have fewer editing and/or formatting functions available than the interface illustrated in FIGS. 4-6.

In some embodiments, a user may open the acquired images in an advanced image analysis software package such as QLab™. The user could make more advanced measurements or analysis on the acquired images. For example, the user may analyze cardiac output and/or movement. These additional findings made in the image analysis software may also be automatically linked to the anatomical illustration in the diagnostic report.

FIGS. 8-11 illustrate through screen shots a method of adding a marker to the rendered anatomical illustration from an acquired ultrasound image. The marker may be made during or after an imaging exam. In this illustrative example, a sonographer "drops a pin." That is, the sonographer adds a free form text comment to an acquired image, and a marker in the shape of a pin is added to the rendered anatomical illustration, linking the text comment and corresponding image to the anatomical illustration. A pin without a comment may also be added to mark an area of interest within the patient's anatomy as determined by the sonographer or physician's findings during an ultrasound exam. A similar method may be used for linking measurements or other findings to the anatomical illustration.

Figure 8:
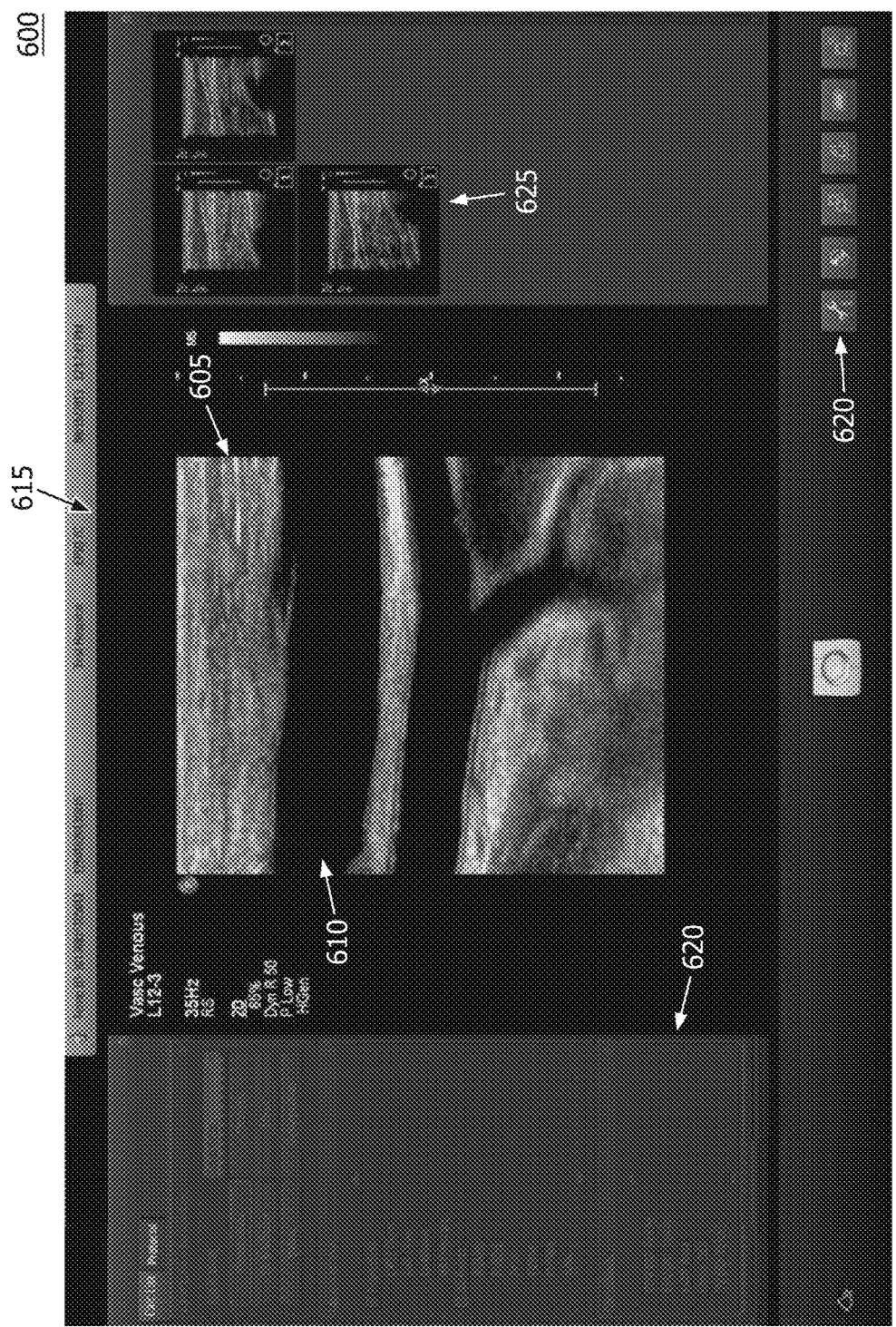
FIG. 8 is a screen shot of a user interface of an ultrasound system according to an embodiment of the present system.

FIG. 8 is a screen shot 600 of an interface for an ultrasound imaging system, such as the one illustrated in FIG. 1. Patient and exam information fields 615 may be displayed. The sonographer may have additional controls 620 displayed for modifying and/or analyzing the images and/or for controlling the imaging system. Previously acquired images 625 may also be displayed. In this example, the sonographer has acquired a 2D image 605 of a blood vessel 610.

Figure 9:
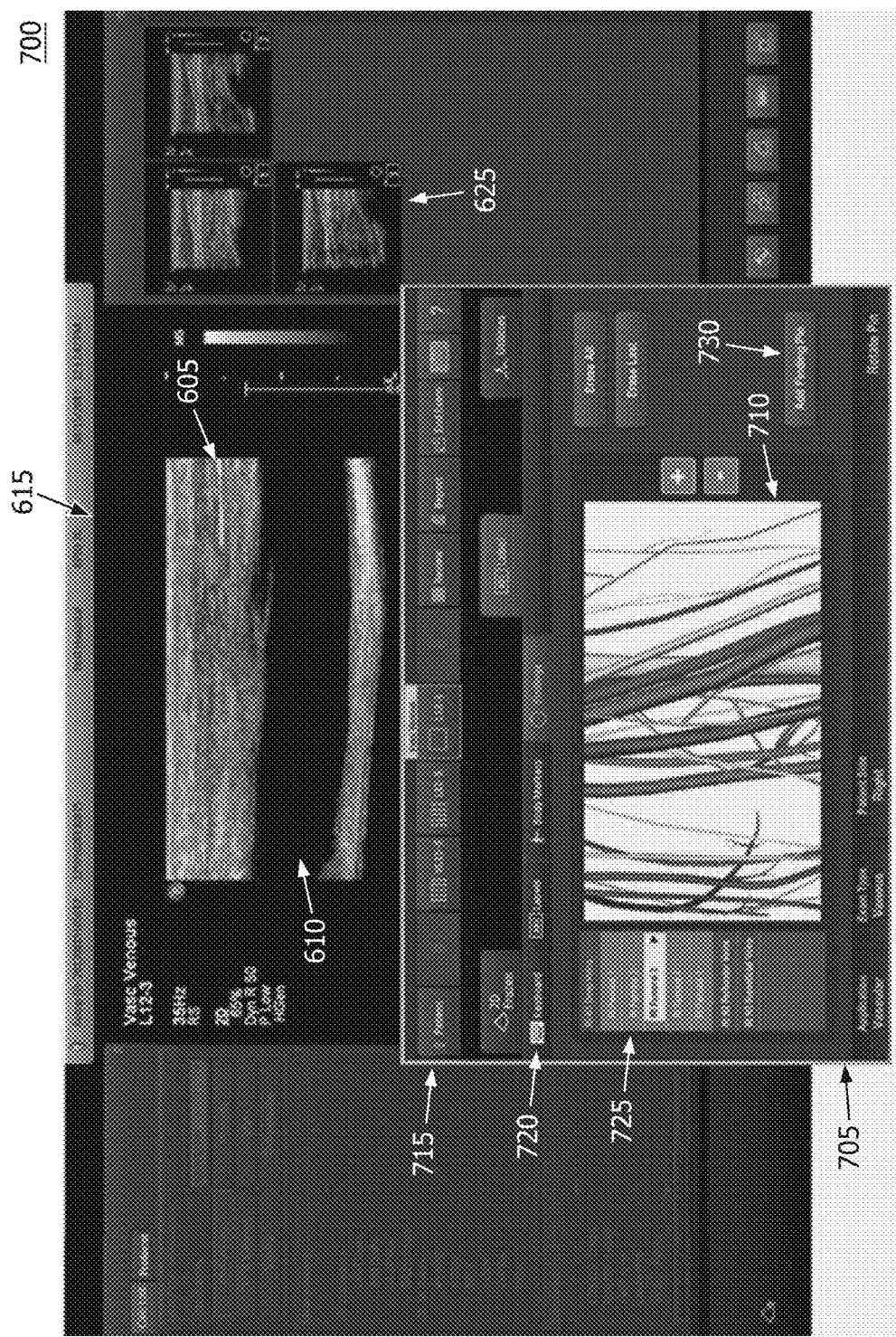
FIG. 9 is a screen shot of a marker interface with the user interface of the ultrasound system shown in FIG. 6 according to an embodiment of the present system.

The sonographer opens a marker interface 705 shown in screen shot 700 in FIG. 9, which controls linking measurements and/or findings in the acquired image to the rendered anatomical illustration. The marker interface 705 may provide controls 715 for the type of image or view acquired. The marker interface 705 may further provide tabs 720 for different types of markers that may be linked with the acquired image or with other portions of the diagnostic report. In this example, the sonographer has selected the Findings tab. A view of the anatomical illustration 710 that corresponds to the anatomy in the acquired image 605 is displayed. The imaging system may automatically determine which location in the anatomical illustration 710 corresponds to the anatomical location in the acquired image 605. The sonographer may override or provide the anatomical location using the toolbar 725. To drop a pin, the sonographer selects the "Add Finding Pin" button 730.

Figure 10:
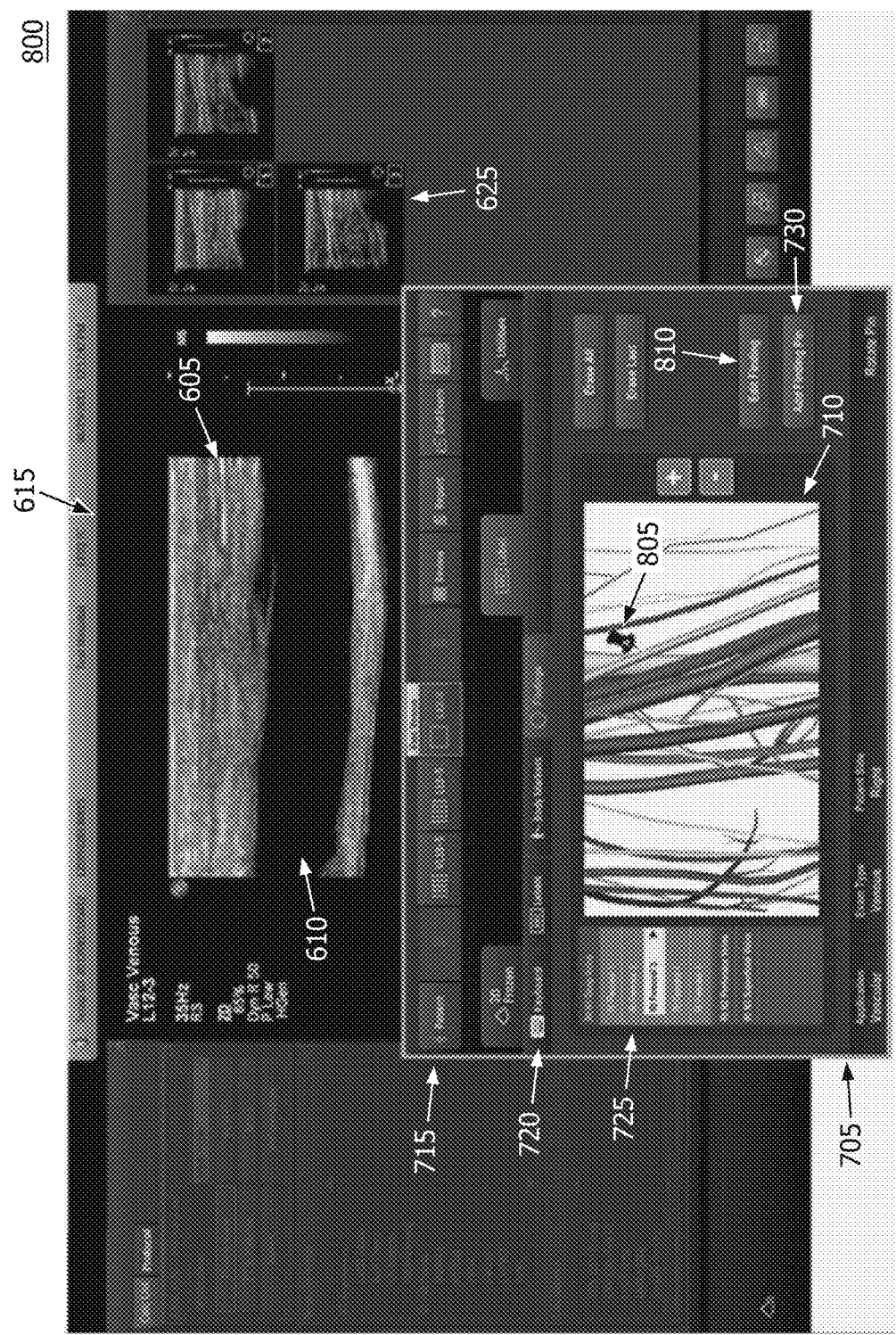
FIG. 10 is another screen shot of the marker interface shown in FIG. 7 according to an embodiment of the present system.
Figure 11:
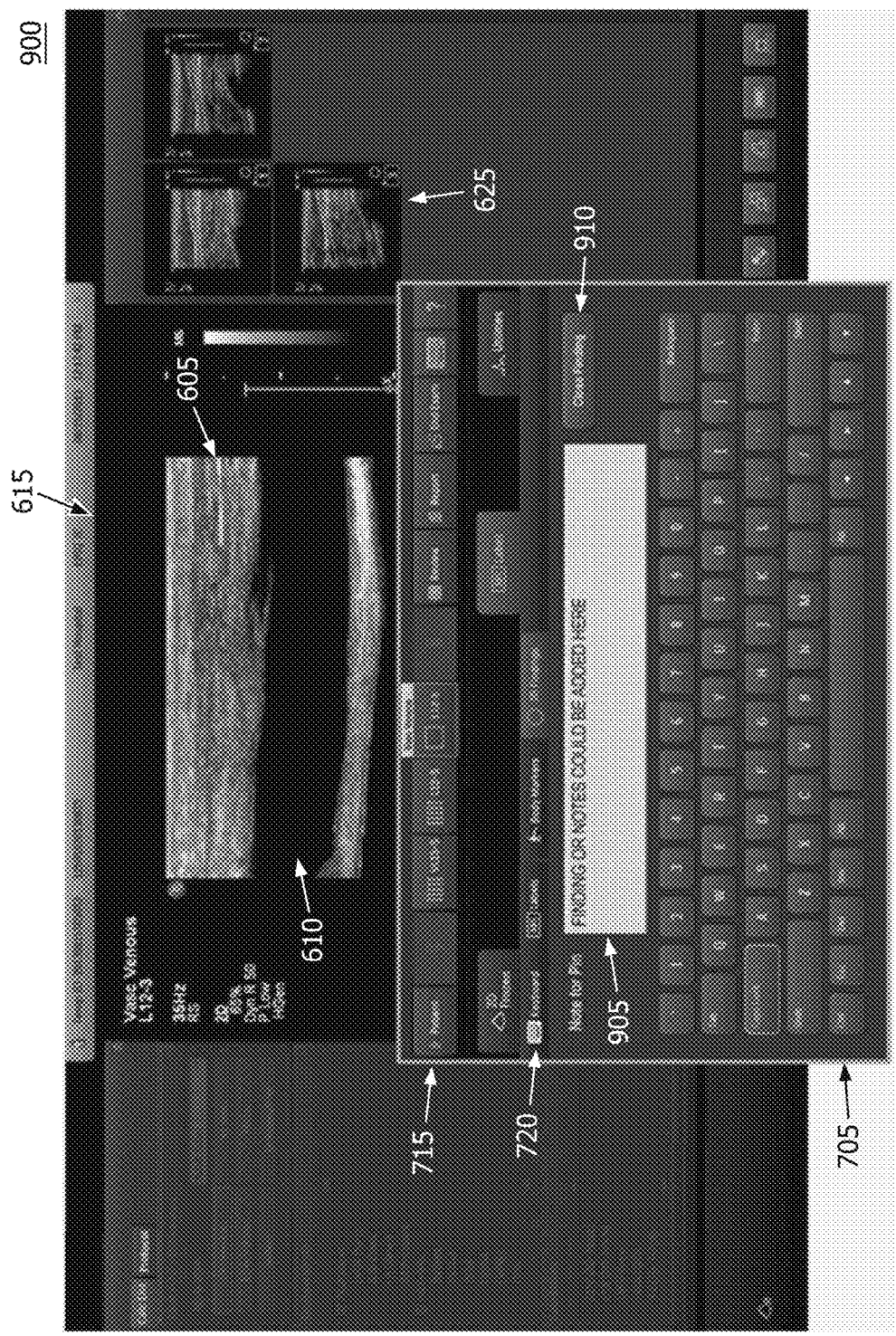
FIG. 11 is a further screen shot of the marker interface shown in FIG. 7 according to an embodiment of the present system.

In the screen shot 800 shown in FIG. 10, the finding pin 805 has been dropped in the desired location. The imaging system has linked the finding pin 805 shown in the anatomical illustration 710. A new "Edit Finding" button 810 now appears. The sonographer may select button 810 to access the text editing interface shown in screen shot 900 in FIG. 11. The sonographer may enter the text through the user control panel 38 or by other means. The text entered by the sonographer will appear in textbox 905. Once the sonographer has completed entering the desired text, the sonographer may select the "Close Finding" button 910 to return to the previous screen as shown in FIG. 10. This process may be repeated for multiple pins, or a similar process may be completed for linking a measurement and/or finding. There may be multiple markers associated with the same acquired image 605. Conversely, there may be multiple acquired images associated with a marker in the rendered anatomical illustration 710. Once the sonographer has completed acquiring images, making measurements, and/or making findings, the anatomical illustration portion of the diagnostic report has been automatically generated by the imaging system. These illustrations may take the form of 2D and/or 3D representation or modifications of anatomical structures, anomalies, pathology variations, or deposits in the patient's anatomy. The illustration portion of the diagnostic report may be accessed via the imaging system, or the data may be transferred to another computer capable of reading the diagnostic report information.

The examples described in reference to FIGS. 2-11 are meant only as clarifying examples of embodiments of the invention and should not be interpreted as limiting the scope of the invention. Other imaging modalities, graphical symbols, user interface layouts, and marker types may be used.

Figure 12:
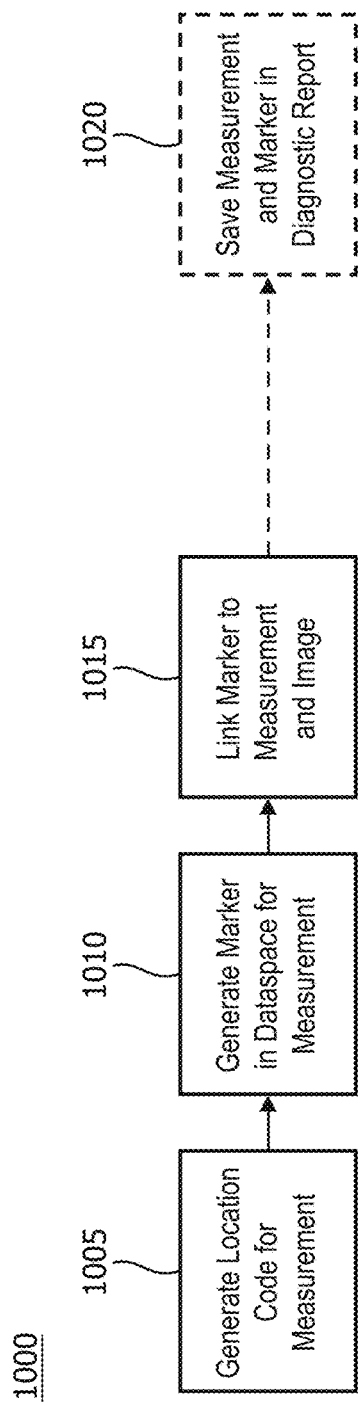
FIG. 12 is a block diagram of a process performed according to an embodiment of the present system.

FIG. 12 is a block diagram of a process 1000 completed by the anatomical information processor 34 when a measurement is made on an acquired image, such as the process shown in FIG. 2. The anatomical information processor 34 may generate computer-readable code that identifies the anatomical location of the measurement based on the spatial and anatomical data at 1005. The spatial and anatomical data may be generated dynamically by the imaging system or stored in the anatomical and spatial database storage 46, such as DICOM compliant data. The anatomical information processor 34 may then convert the location code from step 1005 into a marker containing location information at a corresponding location in a dataspace at 1010 using data associated with the dataspace stored in the dataspace information storage 48. The anatomical information processor 34 may then provide a link between the marker generated at step 1010 with the measurement and the acquired image where the measurement was taken at 1015. Optionally, the anatomical information processor 34 may save the measurement and marker in the diagnostic report storage 50 at 1020. In some embodiments, a user may prevent the anatomical information processor 34 from performing step 1020 if they wish to reacquire the image and/or repeat a measurement. A similar process to that of process 1000 is performed for findings entered by the user, such as plaques or dropped pins, as illustrated in FIGS. 8-11.

Figure 13:
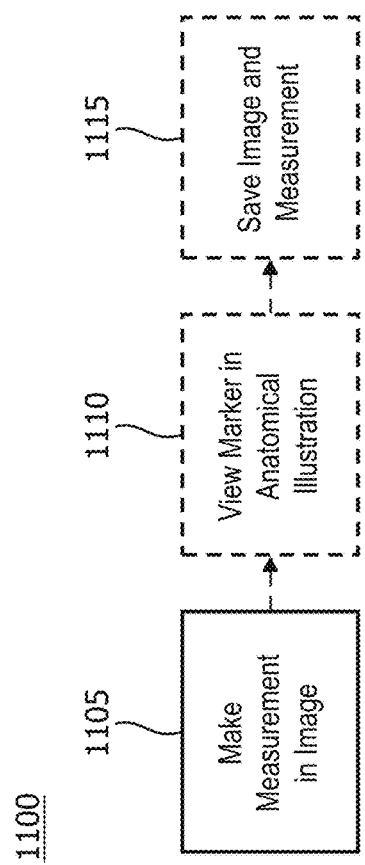
FIG. 13 is a block diagram of a further process performed according to an embodiment of the present system.

FIG. 13 is a block diagram of a process 1100 performed by a user of the system in accordance with the teachings of the disclosure. The user may make a measurement in an image at 1105 using a user interface, such as the user interface 30 of the imaging system in FIG. 1. The user may have acquired the image or the image may have been previously acquired. Step 1105 may be the only required step for a user in some embodiments. The generation of the marker and the linking of the measurement and corresponding image are all performed automatically by the system. Optionally, the user may further view on display 40, or other display, the marker in the anatomical illustration at 1110, and if desired, the user may save the image to report storage 50 or other storage location, which may automatically save the associated measurement and marker. The user may also save the image without previously viewing the anatomical illustration. A similar process is followed for associating findings with acquired images. This process may be less time consuming and allow for more accurate diagnostic reports to be generated. Digital and paper worksheets with drawings of anatomy that require a user to manually complete may be eliminated. This may allow for easier record keeping of patients' exam histories, and allow improved spatial and/or diagnostic correlation between findings and images.

In an embodiment of the invention, a user may be able to open two or more diagnostic reports from different exams and have the markers generated from each report displayed on the same rendered anatomical illustration. The markers may be from images taken with one or more different imaging modalities. The markers may be dated or color-coded to indicate which exam the marker is associated with, but other indicators may be used. This may facilitate tracking findings and measurements in a patient over time and improve diagnosis or treatment. It may also assist in comparing results from two different imaging modalities.

According to the principles of the present invention, the anatomical information processor 34 may be capable of interpreting the spatial and anatomical data from the acquired image and changing the dataspace to reflect the anatomy in the acquired image. For example, a heart image may be acquired from a patient with an abnormally sized left ventricle. The anatomical information processor 34 may alter the data in the dataspace associated with the heart to reflect this information. Accordingly, when the graphics processor 36 renders the anatomical illustration in the diagnostic report, the heart in the illustration may be rendered to have the abnormally sized left ventricle. This may provide better understanding of anatomical irregularities for a physician rather than an imaging technician linking the acquired heart images to the anatomical illustration with a notation of the irregularity.

Although not always shown, the screens 200, 300, 400, 500, 600, 700, 800, and/or 900 may also illustrate user selections which may include, for example, icons or menu items which may be selected by the user to, for example, scan, file, print, transfer images (e.g., from one display to another), mute, transcribe, and/or use a headpiece, as desired. Further, one or more menus as is known in the art may be provided for a user's convenience. The displayed images and associated data may be saved at any time during the processes shown in FIGS. 2, 3, 12, 13 or during subsequent physician analysis. However, a history mode may be activated to gather information indicative of when data may have been added and/or edited so that a user may refer back to original information and/or determine when and/or who made certain changes to information which may be saved in, for example, a generated report. Further, the changes may also be stored for later use.

Although the present system has been described with reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system.

Further, the present systems, apparatuses, and methods, may also be extended to any small parts imaging where the clear landmarks can be defined and reproduced. Further, the present methods may be embedded in a program code which may be applied to existing imaging systems such as, for example, ultrasonic imaging systems. Suitable ultrasonic imaging systems may include a Philips ultrasound system which may, for example, support a conventional broadband linear array transducer that may be suitable for small-parts imaging. Further, analysis techniques such as, for example, QLAB™ may be available on-cart with an imaging apparatus or as a post-processing program which may be run outside of an examination room. Further, multiple nodules, anatomical entities such as follicles, or other detectible objects, may be marked using the present system. Further, the method of the present systems may be applied to volumes acquired using transducers such as, for example, 2D array transducers, which may include, for example, X-matrix™ or mechanical transducers.

Certain additional advantages and features of this invention may be apparent to those skilled in the art upon studying the disclosure, or may be experienced by persons employing the novel system and method of the present invention, chief of which is that a more reliable image acquisition system and method of operation thereof is provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A medical imaging system comprising:
a first non-transitory computer readable storage medium containing a plurality of ultrasound images and spatial data associated with each of the plurality of ultrasound images;
a second non-transitory computer readable storage medium containing a dataspace comprising data representing an anatomical model from which renderings of the anatomical model from different perspectives can be generated; and
a processor configured to:
receive the spatial data from the first non-transitory computer readable storage medium; and
for each of the plurality of ultrasound images, generate a respective marker in the dataspace, wherein each of the respective markers links the spatial data associated with the respective ultrasound image to the data representing the anatomical model such that changing a viewing perspective of the rendering of the anatomical model does not change a spatial location of the marker with respect to the anatomical model.

2. The medical imaging system of claim 1, wherein the marker links data associated with a measurement obtained from the ultrasound image to a corresponding spatial location of the anatomical model.

3. The medical imaging system of claim 2, wherein the processor is further configured to modify dimensions of the anatomical model according to the measurement obtained from the ultrasound image.

4. The medical imaging system of claim 1, wherein the processor is further configured to modify the anatomical model, based at least in part, on the spatial data associated with the image.

5. The medical imaging system of claim 1, wherein the marker links data associated with three-dimensional findings or anatomical visualization notes associated with the ultrasound image to one or more corresponding locations of the anatomical model.

6. A method of linking data in a medical imaging system, the method comprising:
receiving spatial data associated with one or more ultrasound images;
for each of the one or more ultrasound images, generating a respective marker in a dataspace comprising data associated with an anatomical model that represents human anatomy, wherein each of respective markers links a measurement or finding based on the respective ultrasound image to a corresponding spatial location of the human anatomy, the measurement being selected from the group comprising of a width of a blood vessel in the image.

7. The method of claim 6, wherein the method further comprises modifying dimensions of the anatomical model to reflect the measurement.

8. The method of claim 6, further comprising modifying data in the dataspace based, at least in part, on the spatial data associated with the one or more ultrasound images.

9. The method of claim 6, further comprising:
rendering an illustration of the human anatomy from the data of the dataspace; and
displaying the illustration, with a display, wherein the respective markers are displayed on the illustration at the corresponding spatial locations of the human anatomy.

10. The method of claim 9, further comprising updating the rendering of the illustration to display the human anatomy from a different viewing perspective without changing the corresponding spatial locations of the respective markers relative to the human anatomy.

11. The method of claim 6, further comprising:
generating a diagnostic report, wherein the diagnostic report includes the one or more ultrasound images and the respective markers.

12. The method of claim 11, wherein the diagnostic report comprises an illustration of the human anatomy having dimensions that are based at least in part on the one or more ultrasound images.

* * * * *